US009652874B2

(12) United States Patent
Zigon et al.

(10) Patent No.: US 9,652,874 B2
(45) Date of Patent: May 16, 2017

(54) METHOD AND APPARATUS FOR DISPLAYING MULTIDIMENSIONAL DATA (75) Inventors: Robert J. Zigon, Carmel, IN (US); Larry Meyers, Greenfield, IN (US); Tanmay A. Dharmadhikari, Indianapolis, IN (US)

(73) Assignee: Beckman Coulter, Inc., Brea, CA (US)

( * ) Notice: Subject to any disclaimer, the term of this patent is extended or adjusted under 35 U.S.C. 154(b) by 247 days.

(21) Appl. No.: 14/001,155

(22) PCT Filed: Feb. 22, 2012

(86) PCT No.: PCT/US2012/026174
§ 371 (c)(1),
(2), (4) Date: Aug. 22, 2013

(87) PCT Pub. No.: WO2012/138428
PCT Pub. Date: Oct. 11, 2012

(65) Prior Publication Data
US 2013/0328881 A1    Dec. 12, 2013

Related U.S. Application Data (60) Provisional application No. 61/445,944, filed on Feb. 23, 2011.

(51) Int. Cl.
*G06T 11/20*    (2006.01)
*G01N 15/14*    (2006.01)
(52) U.S. Cl.
CPC ........ *G06T 11/206* (2013.01); *G01N 15/1429* (2013.01); *G01N 15/1456* (2013.01)
(58) Field of Classification Search
None
See application file for complete search history.

(56) References Cited

U.S. PATENT DOCUMENTS 6,122,628 A    9/2000    Castelli et al.
8,421,796 B2    4/2013    Song et al.
(Continued)

FOREIGN PATENT DOCUMENTS

CN    101364307 A    2/2009
JP    05-197608 A    8/1993
(Continued)

OTHER PUBLICATIONS

Xiaoquan et al., "Unbiased converted measurements for tracking," Aerospace and Electronic Systems, IEEE Transactions on vol. 34, No. 3, pp. 1023-1027, Jul. 1998.*
(Continued)

*Primary Examiner* — Ke Xiao
*Assistant Examiner* — Jed-Justin Imperial
(74) *Attorney, Agent, or Firm* — K&L Gates LLP; Louis C. Cullman; Thomas A. Turano (57) ABSTRACT A method and apparatus for displaying and manipulating the rendering of multiple parameters obtained from a plurality of objects simultaneously. In one embodiment, the method includes the steps of: plotting the parametric locations of the plurality of objects in m-dimensional parametric space on a first 2-dimensional display; positioning a closed boundary over a subset of the parametric locations of the plurality of objects in the first 2-dimensional display; and plotting the parametric locations of the objects corresponding to the subset of the parametric locations in the first 2-dimensional display in an n-dimensional space on a second 2-dimensional display.

20 Claims, 5 Drawing Sheets (56) References Cited

U.S. PATENT DOCUMENTS

| | | |
|---|---|---|
| 2002/0171646 A1 | 11/2002 | Kandogan |
| 2005/0007383 A1* | 1/2005 | Potter et al. .................. 345/619 |
| 2010/0058222 A1* | 3/2010 | Bergstrom ............. G06T 19/00 715/782 |

FOREIGN PATENT DOCUMENTS

| | | |
|---|---|---|
| WO | 2005/008596 A2 | 1/2005 |
| WO | 2012138428 | 10/2012 |

OTHER PUBLICATIONS

Fanea et al., "An interactive 3D integration of parallel coordinates and star glyphs," IEEE Symposium on Information Visualization, 2005. INFOVIS 2005., 2005, pp. 149-156.*

Kaluza—Flow Cytometry Analysis Software 1-20—Instructions for Use 11 Sep. 1, 2009 (Sep. 1, 2009). XP55040331. Beckman Coulter. Inc. Brea. CA. USA.

International Search Report for international application PCT/US2012/026174 filed on Feb. 22, 2012.

\* cited by examiner

METHOD AND APPARATUS FOR DISPLAYING MULTIDIMENSIONAL DATA

PRIORITY CLAIM

This application claims the benefit under 35 U.S.C. §371 of PCT/US2012/026174 filed Feb. 22, 2012 which claims priority to U.S. Provisional Patent Application U.S. 61/445,944, filed Feb. 23, 2011, the entire contents of each of which are hereby incorporated by reference.

FIELD OF INVENTION

This invention relates to the field of data analysis and more specifically to a method and device for displaying and manipulating multidimensional data from an instrument such as a flow cytometer.

BACKGROUND

Multiple measurements performed on a single sample have been a problem if the user wanted to see more than three parameters displayed together simultaneously. While the relationships of two or three parameters are easily plotted as two or three dimensional graphs respectively, larger numbers of parameters remain somewhat difficult to simultaneously display and view by a user.

Multiple parameters have been plotted in two dimensional space through the use of non-orthogonal display axes. Users become accustomed to understanding the relationships of objects plotted on multi-parameter graphs, and the ability to view subsets of the data and relationships between the various parameters. However, other than the simple rotation of display axes, the manipulation of the multiple parameter display of such data to better permit the user to see the relationships between the parameters has remained somewhat problematic. What is needed is a system to better permit a user to display and manipulate the display of multidimensional data.

The present invention addresses these issues.

SUMMARY OF THE INVENTION

The invention relates in part to a method and apparatus for rendering and manipulating the display of multiple parameters obtained from a plurality of objects simultaneously.

In one aspect, the invention relates to a method of displaying multidimensional data relating to a plurality of objects. In one embodiment, the method includes the steps of plotting, by a processor on a display device the parametric locations of the plurality of objects in m-dimensional parametric space on a first 2-dimensional display and positioning a boundary over a subset of the parametric locations of the plurality of objects in the first 2-dimensional display on the display device. In another embodiment the method further comprises the step of performing data analysis on the objects within the boundary. In another embodiment the step of performing data analysis comprises plotting, by the processor on the display device, the parametric locations of the objects corresponding to the subset of the parametric locations in the first 2-dimensional display in an n-dimensional space on a second 2-dimensional display.

In another embodiment, the method further includes the step of reading the multiparameter object data from a storage device. In yet another embodiment, the method further includes the step of reading the multiparameter object data from an instrument. In still yet another embodiment, the method further includes the step of translating the origin of the second 2-dimensional display. In one embodiment, the method includes the step of reorienting the axes of the second 2-dimensional display. In another embodiment, the method includes the step of calculating object parametric data from object measured data.

In another aspect, the invention relates to a system of displaying multidimensional data relating to a plurality of objects. In one embodiment, the system includes a display device; a user input device; and a processor, in communication with the display device and the user input device. The processor plots the parametric locations of the plurality of objects in m-dimensional parametric space on a first 2-dimensional display. The system positions a closed boundary over a subset of the parametric locations of the plurality of objects in the first 2-dimensional display on the display device. The processor plots on the display device the parametric locations of the objects corresponding to the subset of the parametric locations in the first 2-dimensional display in an n-dimensional space on a second 2-dimensional display.

In another embodiment, the system further includes a data storage device in communication with the processor, from which the processor reads object data. In another embodiment, the system further includes a second display device for displaying the second 2-dimensional display.

In yet another aspect, the invention relates to a method for displaying multidimensional data from a plurality of objects. In one embodiment, the method includes the steps of: for each object having multidimensional data, generating, using a processor, a location in m-dimensional parameter space; transforming, using a processor, a location in n≤m-dimensional parameter space for each object; plot, on a display device, an n-dimensional location for each object in m-dimensional parameter space onto a first 2-dimensional geometric display space; defining, on the display device, a closed boundary in the first 2-dimensional geometric display space; positioning, on the display device, the closed boundary over a subset of the parametric locations of the objects in the first 2-dimensional geometric display space; transforming, by the processor, a location in p≤m-dimensional parameter space for each object whose parameters are within the closed boundary; and plotting, on a second display device, in a second 2-dimensional display space the p-dimensional location for each object within the boundary in the first 2-dimensional geometric display space.

In another embodiment, the method further includes the step of reading, by the processor from a data storage device, multidimensional data from the plurality of objects. In yet another embodiment, the second display device and the first display device are the same display device. In still yet another embodiment, the method further includes the step of selecting the shape of the closed boundary.

In still yet another aspect, the invention relates to a method for displaying multidimensional data from a plurality of objects. In one embodiment, the method includes the steps of, for each object having multidimensional data, and for each event associated with each object, and for each dimension to be displayed, transforming, using a processor, an event location in m-dimensional parameter space for each object using the algorithmic relationships: $X=X+(eventValue*COS(axisAngle)*axisRadius)$ and $Y=Y+(eventValue*SIN(axisAngle)*axisRadius)$, wherein eventValue is the numerical value of the event, axisRadius is the length of the axis and axisAngle is the angle of the axis in the display; and defining, on the display device, a closed boundary in a first 2-dimensional geometric display space; positioning, on the display device, the closed boundary over a subset of the parametric locations of the objects in the first 2-dimensional geometric display space; and determining if the transformed event location is within the closed boundary; and if the event location is within the closed boundary flagging the event.

BRIEF DESCRIPTION OF THE DRAWINGS

The objects and features of the invention can be better understood with reference to the drawings described below. The drawings are not necessarily drawn to scale; emphasis is instead being placed on illustrating the principles of the invention. The drawings associated with the disclosure are addressed on an individual basis within the disclosure as they are introduced.

DETAILED DESCRIPTION

The following description refers to the accompanying drawings that illustrate certain embodiments of the invention. Other embodiments are possible and modifications may be made to the embodiments without departing from the spirit and scope of the invention. Therefore, the following detailed description is not meant to limit the invention. Rather, the scope of the invention is defined by the appended claims.

It is important to realize that this data analysis technique and system is not limited to any type of data or data from any type of specific device that measures multiple parameters, either directly or computationally. Solely for the purposes of explanation, the description of the embodiments of the invention will reference data from a flow cytometer, but the invention is not restricted to such an instrument or the data it produces.

For the purposes of explanation, and in brief overview, a flow cytometer as known to the art includes a source of biological cells or other analytes, a laser, a plurality of photodetectors and a processor system. The source of cells moves the cells in a linear fashion through a channel. As the cells pass through the channel they intersect a beam of light from the laser and light is typically scattered in the forward (FS) direction and in the side directions (SS). Light scattered in the forward direction is an indication of cell size while light scatter in the side direction is an indication of cell complexity. If the cells have been stained with a fluorescent dye and the dyes are chosen so as to be excited by the laser light, fluorescent light from the dyes is also emitted.

The forward and side scattered light is detected by detectors placed in the path of and orthogonal to the path of the laser light beam, respectively. Similarly, fluorescent light is detected by one of a plurality of photodetectors, again orthogonally placed to the path of the laser beam. Signals obtained from the photodetectors are digitized by the processor system, stored on disk and displayed. The data on the disks can then be analyzed and displayed by other processor systems.

Figure 1:
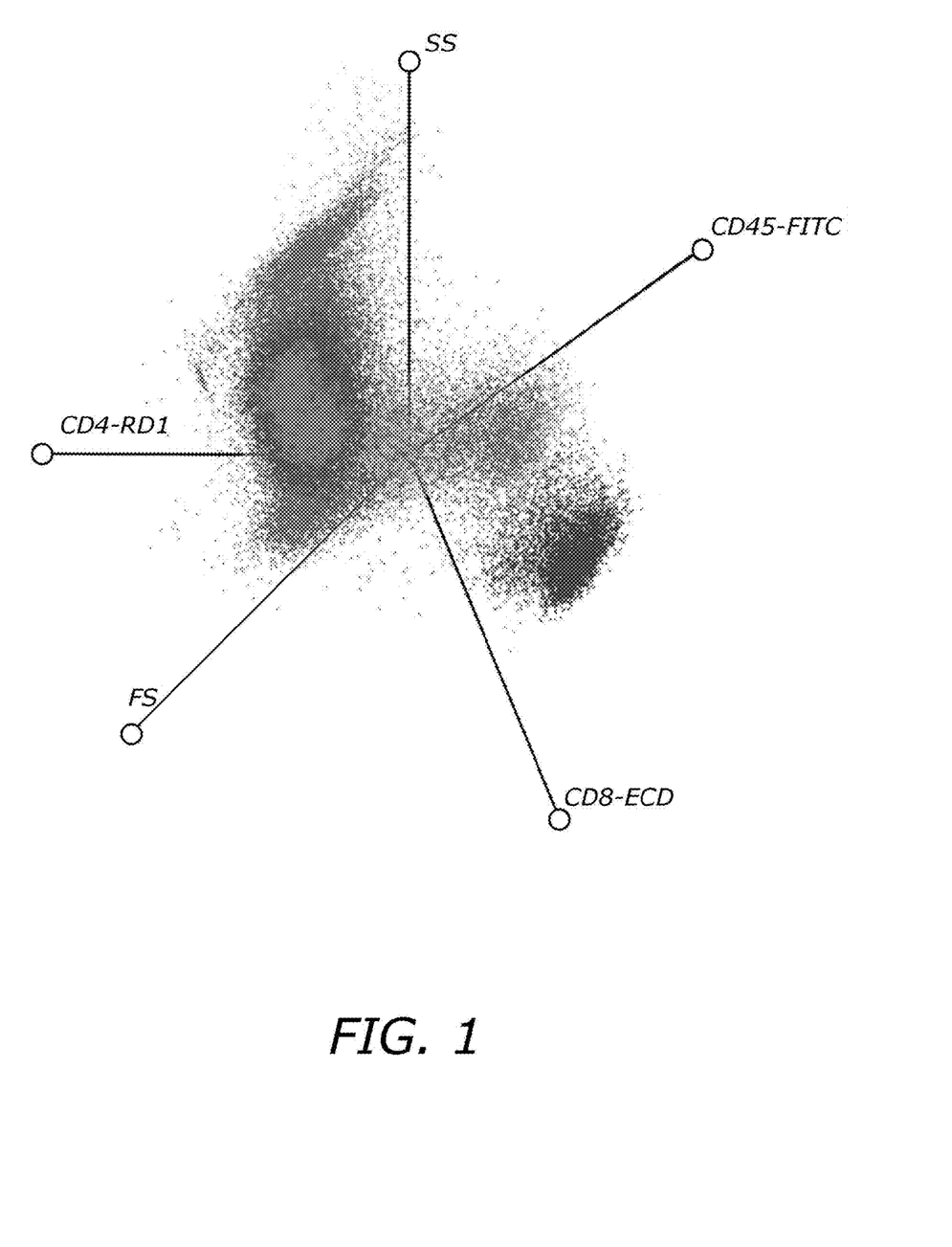
FIG. 1 is an embodiment of a 2-dimensional display of a five dimensional plot of flow cytometry data.
Figure 2:
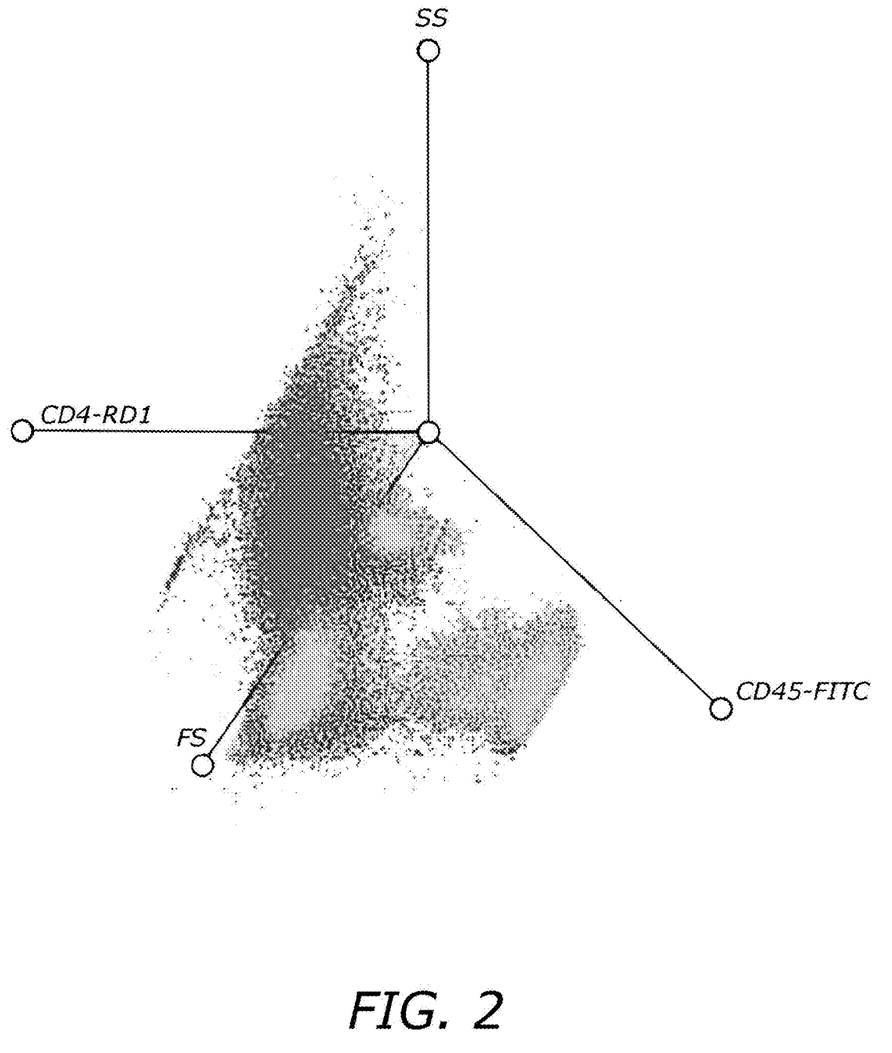
FIG. 2 is an embodiment of a 2-dimensional display of a four dimensional plot of flow cytometry data.

If the cells are stained with a number of dyes and each dye has a peak which is detected by a different detector, a multidimensional scatter plot of the cells can be drawn (FIG. 1). As seen in FIG. 1, each axis of the multidimensional scatter plot corresponds to a different parameter (forward scattering, side scattering) or monoclonal antibody with fluorescent-dye (CD45-FITC, CD4-RD1, and CD8-ECD). The plot shown displays five parameters for simplicity but more parameters could have been displayed. Generally with such plots one can select more or fewer parameter axes to plot. FIG. 2 depicts a replotting of FIG. 1 with only four axes plotted. The system can produce statistical calculations on the entire dataset or portions of the datasets as selected and plotted or not plotted by the user.

Figure 3:
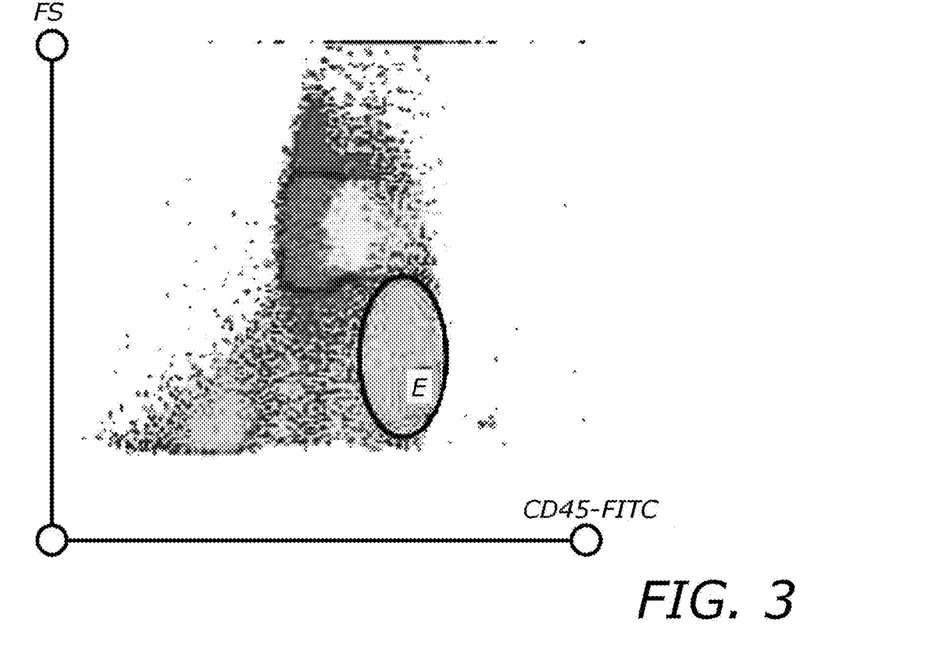
FIG. 3 is another embodiment of a 2-dimensional display of a two dimensional plot of flow cytometry data showing the selection of flow cytometric data using a closed boundary of the invention.

To make the explanation of the operation of the system of the invention easier, consider an initial multidimensional data set for which initially only two of the dimensions are displayed in a scatter plot (FIG. 3). In this plot, the forward scatter or size measurement is measured against the amount of fluorescent label CD45-FITC on the cells. To allow the user to select points of interest, in this case corresponding to cells which are of a certain size and which have a certain amount of fluorescence, the system provides a closed boundary, in this case an ellipse (E), on the display. The user of the system, by placing the ellipse (E) over an area of the scatter plot using an input device such as a mouse, selects a region of the scatter plot that is of interest. Alternatively, the system may select the regions of interest without user intervention. Although in this example the closed boundary is an ellipse, any shape boundary can be used. Typically the boundary is a closed boundary but may be an open boundary if the boundary is positioned at the edge of the display area.

Figure 4:
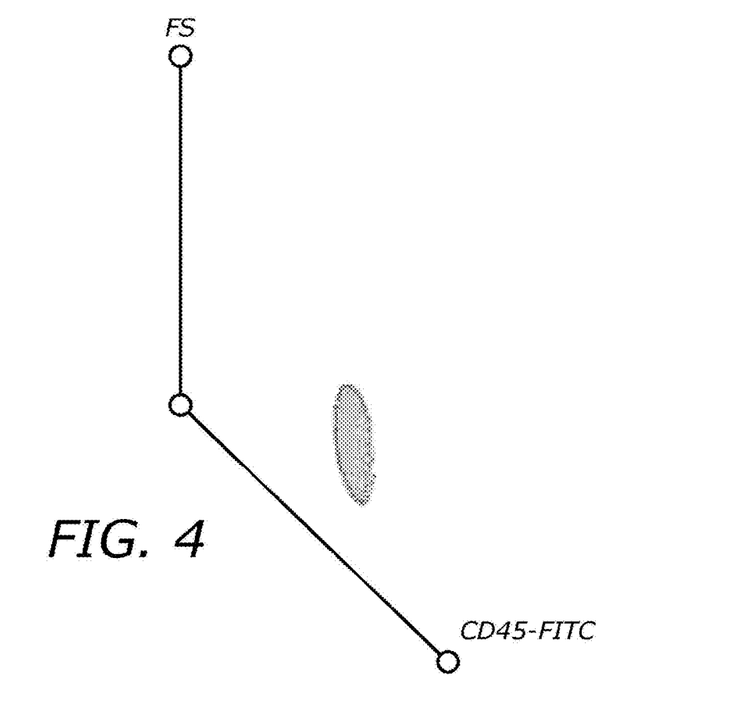
FIG. 4 is yet another embodiment of a plot of flow cytometry data selected by the closed boundary of FIG. 3 and displayed on a second multidimensional plot as a 2-dimensional display.
Figure 5:
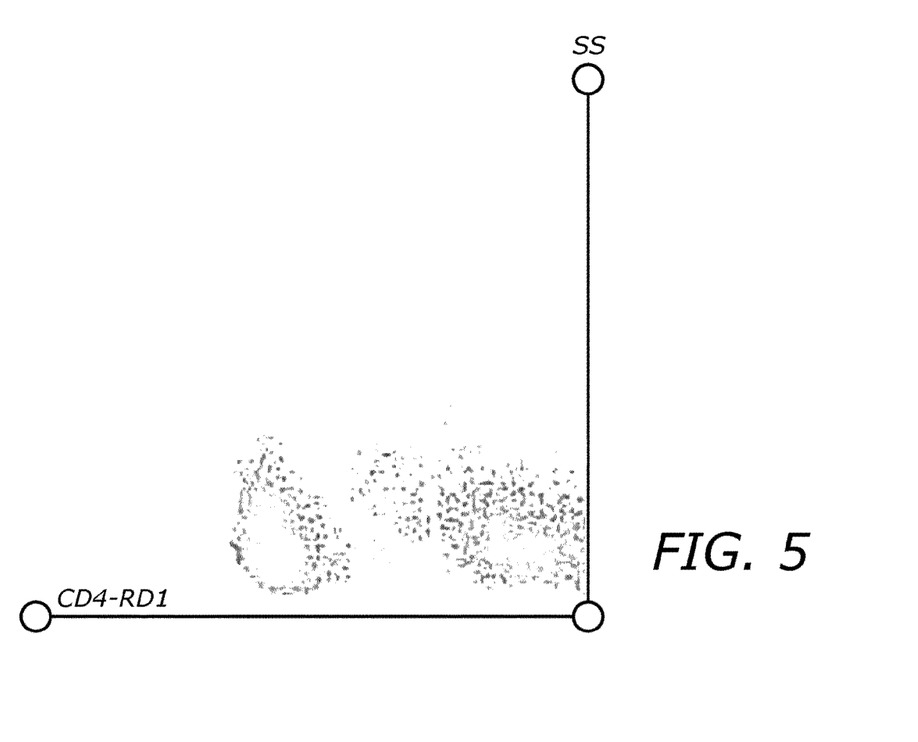
FIG. 5 is still yet another embodiment of a plot of flow cytometry data selected by the closed boundary of FIG. 3 and displayed on a second multidimensional plot as a 2-dimensional display.
Figure 6:
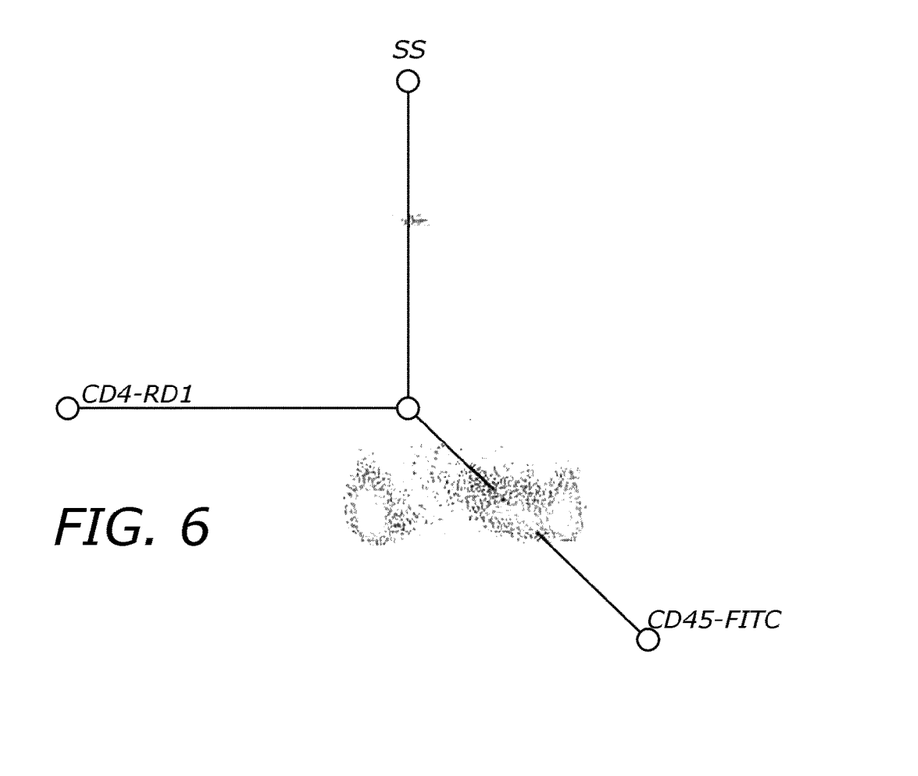
FIG. 6 is another embodiment of a plot of flow cytometry data selected by the closed boundary of FIG. 3 and displayed on another multidimensional plot as a 2-dimensional display.

The user can then ask the system to replot parameters of the objects of interest in the area of interest (E) of the full scatter plot onto another plot of the same parameters for the objects FIG. 4 or another multidimensional plot of different parameters of the same objects FIG. 5. Alternatively, the user can choose not to replot the data selected within the boundary, but instead simply perform data analysis such as statistical analysis and graphing without resorting to scatter plots. In FIG. 4 the region of interest defined by the ellipse is mapped to the same parameter space from which the data is selected but the axes have been repositioned. Alternatively those objects, in this example the cells measured by flow cytometry, which correspond to the parameters in the ellipse, can be remapped to an entirely different parameter space as in FIG. 5. In FIG. 5, the fluorescent component of the monoclonal CD4-RD1 is mapped against the side scattering or complexity of the cell. Note that this is not simply a remapping of the same parameters because neither axis in FIG. 5 (SS side scattering or CD4-RD1) is in FIG. 4. Finally, FIG. 6 plots three parameters (SS side scattering, monoclonal antibody CD4-RD1, and monoclonal antibody CD45-FITC) of the cells of interest from the bounded region in FIG. 3 in 2-dimensional space.

It is important to realize that FIGS. 1-6 do not represent three dimensional views. That is, the axes of FIGS. 1-6 are not the edges of a cube, but instead represent 2-dimensional plots of various axes of a multidimensional space. The orientation, length and axes of these plots are selectable by the user in an interactive manner.

Figure 7:
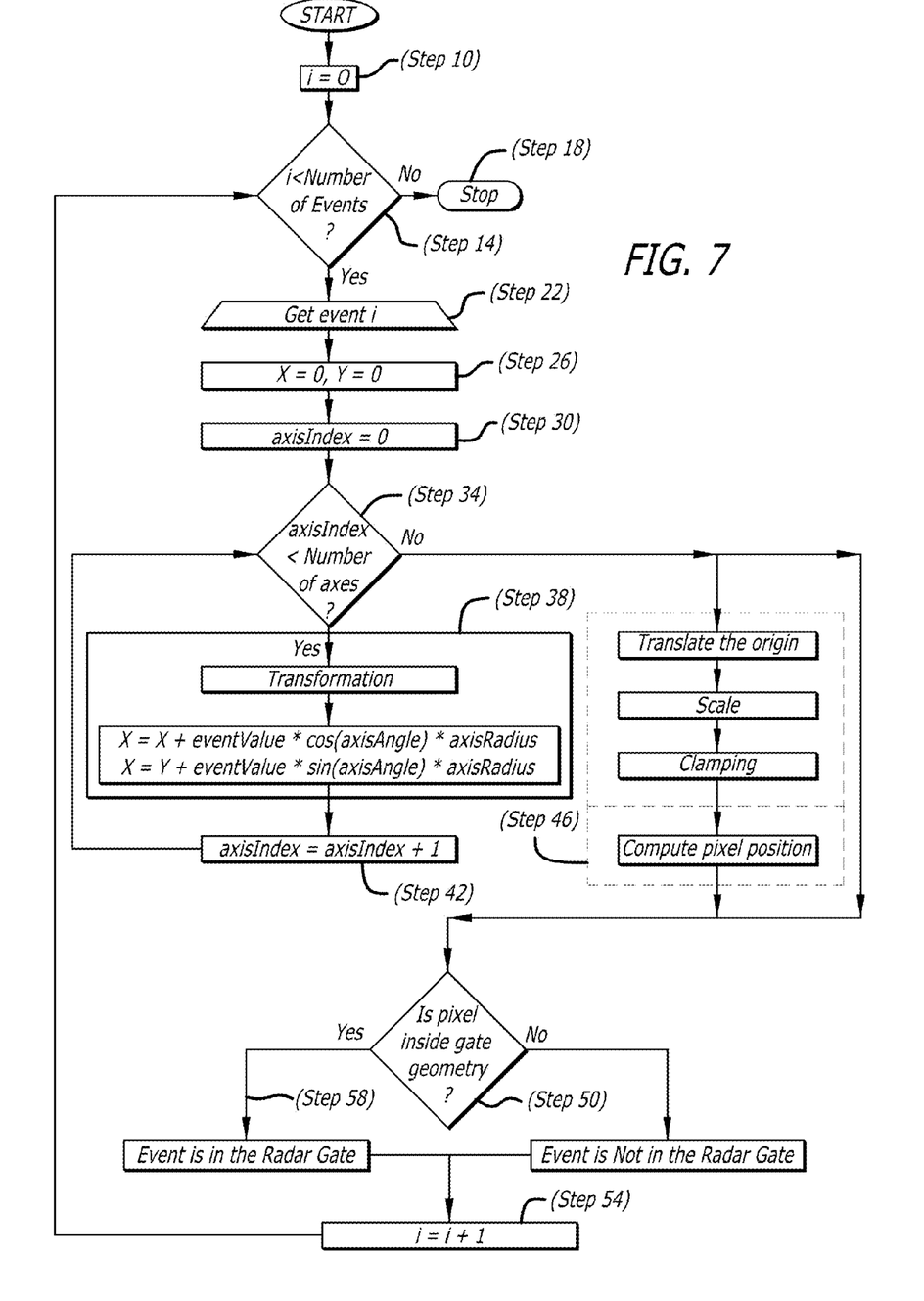
FIG. 7 is a flow chart of an embodiment of the algorithm of the invention.

Referring to FIG. 7, to accomplish this user adjustable flexibility of display, the system, which includes a processor, data storage device, user input device and a display device, executes an algorithm as shown in the figure. For the purposes of discussion herein, when the word "processor" or "processor system" is used, the intent is that such words encompass and are not limited to stand-alone processors, but also microprocessors, field programmable gate arrays, personal computers, tablets, and specially constructed electronic circuits. The system accesses the object parameter data set either from a data storage device or from the measuring instrument directly.

In this FIG. 7, the term "event" means the collection of measurements, actual or calculated, made on an object. The system first sets the "event" or measurement set number (I) equal to zero (Step 10). Then, as part of a loop the system first determines if the "event" value is less than the total number of events (Step 14). If this is not true, then every event (data for all objects) has been plotted and the execution terminates (Step 18).

If the measurement set number (I) is less than the total number of events, then the data from the first event is obtained (Step 22), the plotting variable initialized (Step 26), and the number of axes to be plotted (Step 30) initialized. As long as the number of axes plotted is less than the number of axes displayed (Step 34), the values of the parameters for the event are transformed according to the algorithmic relationship:

$$X = X + eventValue * COS(axisAngle) * axisRadius$$

$$Y = Y + eventValue * SIN(axisAngle) * axisRadius$$

These equations replace X,Y with the previous values of X,Y plus the value of the event times either the cosine value of the axis angle (for X) or the sine value of the axis angle (for Y) times the axis radius. This transformation essentially is a transformation to polar coordinates for plotting purposes, with the origin of the display at the center of the display and the angle measured from what would normally be the X-axis.

The axisIndex is then incremented (Step 42) and the loop repeats until all the various axes are computed. At this point, the position of the point or pixel is calculated on the two dimensional display (Step 46). Next, the system determines if that pixel point is inside the user selected area (E) (Step 50). If the pixel point is not within (E), the event index is simply incremented (Step 54) and the outer loop repeats. If the point is within the user selected area, the event is flagged as being within the set of points of interest (Step 58). Then the system increments the event index (Step 54) and the outer loop repeats. In this way, the objects corresponding to the points within the closed boundary of the parameter plot are determined and are then replotable on another two dimensional display, on the same or different display device, with the parameters of interest. The system may optionally (as shown in phantom in FIG. 7) translate the origin of the plot, and rescale the plot. The clamping function plots points which would normally be off-scale due to axis limitations to the maximum value of the display axis.

It is to be understood that the figures and descriptions of the invention have been simplified to illustrate elements that are relevant for a clear understanding of the invention. Those of ordinary skill in the art will recognize, however, that these and other elements may be desirable. However, because such elements are well known in the art, and because they do not facilitate a better understanding of the invention, a discussion of such elements is not provided herein. It should be appreciated that the figures are presented for illustrative purposes and not as construction drawings. Omitted details and modifications or alternative embodiments are within the purview of persons of ordinary skill in the art.

It can be appreciated that, in certain aspects of the invention, a single component may be replaced by multiple components, and multiple components may be replaced by a single component, to provide an element or structure or to perform a given function or functions. Except where such substitution would not be operative to practice certain embodiments of the invention, such substitution is considered within the scope of the invention.

The examples presented herein are intended to illustrate potential and specific implementations of the invention. It can be appreciated that the examples are intended primarily for purposes of illustration of the invention for those skilled in the art. There may be variations to these diagrams or the operations described herein without departing from the spirit of the invention. For instance, in certain cases, method steps or operations may be performed or executed in differing order, or operations may be added, deleted or modified.

Furthermore, whereas particular embodiments of the invention have been described herein for the purpose of illustrating the invention and not for the purpose of limiting the same, it will be appreciated by those of ordinary skill in the art that numerous variations of the details, materials and arrangement of elements, steps, structures, and/or parts may be made within the principle and scope of the invention without departing from the invention as described in the claims.

Variations, modification, and other implementations of what is described herein will occur to those of ordinary skill in the art without departing from the spirit and scope of the invention as claimed. Accordingly, the invention is to be defined not by the preceding illustrative description, but instead by the spirit and scope of the following claims.

The invention claimed is:

1. A method of displaying multidimensional data relating to a plurality of objects comprising the steps of:
   plotting, by a processor on a display device the parametric locations of the plurality of objects in m-dimensional parametric space on a first 2-dimensional display; and
   positioning a boundary over a subset of the parametric locations of the plurality of objects in the first 2-dimensional display on the display device
   wherein m>3,
   wherein the boundary over the subset of the parametric locations of the plurality of objects traverses o-dimensions of the m-dimensional space,
   wherein o≤m,
   wherein the m-dimensional space is non-planar, and
   wherein the boundary is a 2-dimensional shape in the 2-dimensional display corresponding to an o-dimensional shape in m-dimensional space, wherein the o-dimensions are non-planar.

2. The method of claim 1, further comprising the step of performing data analysis on the objects within the boundary.

3. The method of claim 2, wherein the step of performing data analysis comprises the step of plotting, by the processor on the display device the parametric locations of the objects corresponding to the subset of the parametric locations in the first 2-dimensional display in an n-dimensional space on a second 2-dimensional display.

4. The method of claim 3, further comprising the step of translating the origin of the second 2-dimensional display.

5. The method of claim 3, further comprising the step of reorienting the axes of the second 2-dimensional display.

6. The method of claim 2, wherein the step of performing data analysis further comprises the step of calculating statistics on the multidimensional data corresponding to the subset of the parametric locations in the first 2-dimensional display.

7. The method of claim 2, wherein the step of performing data analysis comprises the step of calculating object parametric data from object measured data.

8. The method of claim 1, further comprising the step of reading the multidimensional data from a storage device.

9. The method of claim 1, further comprising the step of reading the multidimensional data from an instrument.

10. The method of claim 1, further comprising the step of storing the multidimensional data corresponding to the subset of the parametric locations in the first 2-dimensional display to a storage device.

11. A system of displaying multidimensional data relating to a plurality of objects, the system comprising:
   a display device;
   a user input device; and
   a processor, in communication with the display device and the user input device, the processor configured to plot on the display device the parametric locations of the plurality of objects in m-dimensional parametric space on a first 2-dimensional display and configured to position a boundary over a subset of the parametric locations of the plurality of objects in the first 2-dimensional display on the display device,
   wherein m>3,
   wherein the m>3 axes are non-orthogonal,
   wherein the boundary over a subset of the parametric locations of the plurality of objects traverses o-dimensions of the m-dimensional space,
   wherein o≤m,
   wherein the m-dimensional space is non-planar, and
   wherein the boundary is a 2-dimensional shape in the 2-dimensional display corresponding to an o-dimensional shape in m-dimensional space, wherein the o-dimensions are non-planar.

12. The system of claim 11, wherein the processor is configured to select those objects within the boundary.

13. The system of claim 12, wherein the processor is configured to plot on the display device the parametric locations of the objects corresponding to the subset of the parametric locations in the first 2-dimensional display in an n-dimensional space on a second 2-dimensional display.

14. The system of claim 13, further comprising a second display device is configured to display the second 2-dimensional display.

15. The system of claim 12, wherein the processor is configured to perform data analysis on the selected objects within the boundary.

16. A method for displaying multidimensional data from a plurality of objects comprising the steps of:
   for each object having multidimensional data, generating, using a processor, a location in m-dimensional parameter space;
   transforming, using a processor, a location in n≤m-dimensional parameter space for each object;
   plotting, on a display device, an n-dimensional location for each object in m-dimensional parameter space onto a first 2-dimensional geometric display space;
   defining, on the display device, a closed boundary in the first 2-dimensional geometric display space;
   positioning, on the display device, the closed boundary over a subset of the parametric locations of the objects in the first 2-dimensional geometric display space;
   transforming, by the processor, a location in p≤m-dimensional parameter space for each object whose parameters are within the closed boundary; and
   plotting, on a second display device, in a second 2-dimensional display space the p-dimensional location for each object within the boundary in the first 2-dimensional geometric display space,
   wherein the first display device and the second display device display different coordinates,
   wherein m>3,
   wherein the boundary over a subset of the parametric locations of the plurality of objects traverses o-dimensions of the m-dimensional space,
   wherein o≤m,
   wherein the m-dimensional space is non-planar, and
   wherein the boundary is a 2-dimensional shape in the 2-dimensional display corresponding to an o-dimensional shape in m-dimensional space, wherein the o-dimensions are non-planar.

17. The method of claim 16, further comprising the step of reading, by the processor from a data storage device, the multidimensional data from the plurality of objects.

18. The method of claim 16, wherein the second display device and the first display device are the same display device.

19. The method of claim 16, further comprising the step of selecting the shape of the closed boundary.

20. A method for displaying multidimensional data from a plurality of objects, the method comprising the steps of:
   for each object having multidimensional data, and for each event associated with each object, and for each dimension to be displayed,
   transforming, using a processor, an event location in m-dimensional parameter space for each object using the algorithmic relationships: $X=X+(eventValue*COS(axisAngle)*axisRadius)$ and $Y=Y+(eventValue*SIN(axisAngle)*axisRadius)$, wherein eventValue is the numerical value of the event, axisRadius is the length of the axis and axisAngle is the angle of the axis in the display; and
   defining, on the display device, a closed boundary in a first 2-dimensional geometric display space;
   positioning, on the display device, the closed boundary over a subset of the parametric locations of the objects in the first 2-dimensional geometric display space;
   determining if the transformed event location is within the closed boundary; and
   flagging the event if the transformed event location is determined to be within the closed boundary
   wherein m>3,
   wherein the boundary over a subset of the parametric locations of the plurality of objects traverses o-dimensions of the m-dimensional space,
   wherein o≤m,
   wherein the m-dimensional space is non-planar, and
   wherein the boundary is a 2-dimensional shape in the 2-dimensional display corresponding to an o-dimensional shape in m-dimensional space, wherein the o-dimensions are non-planar.

* * * * *